United States Patent
DiGirolamo

(10) Patent No.: US 6,468,510 B2
(45) Date of Patent: Oct. 22, 2002

(54) WAX FREE TRANSPARENT LIPSTICK COMPOSITION

(75) Inventor: Debra DiGirolamo, Holmdel, NJ (US)

(73) Assignee: Cosmetic Essence, Inc., Holmdel, NJ (US)

(*) Notice: Subject to any disclaimer, the term of this patent is extended or adjusted under 35 U.S.C. 154(b) by 0 days.

(21) Appl. No.: 09/754,457

(22) Filed: Jan. 4, 2001

(65) Prior Publication Data

US 2002/0085984 A1 Jul. 4, 2002

(51) Int. Cl.$^7$ .................. A61K 7/025; A61K 6/00; A61K 7/00; A61K 7/06
(52) U.S. Cl. .................. 424/64; 424/401; 424/70.11; 424/70.122
(58) Field of Search .................. 424/64, 401, 70.11, 424/70.122; 514/772.4

(56) References Cited

U.S. PATENT DOCUMENTS

| | | | |
|---|---|---|---|
| 5,266,321 A | | 11/1993 | Shukuzaki et al. |
| 5,362,482 A | | 11/1994 | Yoneyama et al. |
| 5,610,199 A | | 3/1997 | Cohen et al. |
| 5,780,517 A | * | 7/1998 | Cohen et al. .......... 514/721 |
| 5,843,194 A | | 12/1998 | Spaulding |
| 5,843,407 A | | 12/1998 | El-Nokaly et al. |
| 6,063,391 A | * | 5/2000 | Nanba et al. .......... 424/407 |
| 6,183,760 B1 | * | 2/2001 | Travkina et al. ....... 424/401 |

* cited by examiner

*Primary Examiner*—Thurman K. Page
*Assistant Examiner*—Humera N. Sheikh
(74) *Attorney, Agent, or Firm*—Goodwin Procter LLP

(57) ABSTRACT

The invention is a wax free lipstick composition of from about 30 to about 50% wt. tackiness agent, from about 30 to about 50% wt. of an oil or ester, from about 0.01 to about 5% wt. of a firming, bulking agent, from about 0.5 to about 10% wt. of a transparent, oil-gelatinizing agent, and (v) optionally one or more of a coloring, perfuming, and appearance improving additive.

13 Claims, No Drawings

WAX FREE TRANSPARENT LIPSTICK COMPOSITION

FIELD OF INVENTION

The present invention relates to a wax free transparent lipstick composition. As used herein throughout the disclosure and the claims, "transparent" is intended also to include somewhat transparent, but also translucent compositions. Also as used herein throughout the disclosure and the claims, any reference to "lipstick" includes any composition that can be or is intended to be applied to the lips of a user, including cosmetic products such as lip glosses, lip balms and the like.

BACKGROUND

Lipsticks which are designed to color lip surfaces red, are generally highly pigment loaded, red or otherwise colored opaque bodies.

However, "transparent" and low wax lipsticks that are more likely lip glosses, if they are literally transparent, are known from e.g. U.S. Pat. No. 5,610,199 wherein a solid lipophilic composition, based on the lipophilic ingredient dibenzyl monosorbitol acetate (DBMSA) is blended with an alkylbenzoate-containing composition and a glycerol trioctanoate composition to form a transparent base, and then a red pigment is added and the resulting reduced transparency product is poured into a lipstick mold. The purpose of this composition is to utilize DBMSA as a cosmetic base.

Glutamic acid amides are known cosmetic ingredients in the lipstick art. Thus, for example, U.S. Pat. No. 5,843,407 describes a non-sweating, waxy lipstick compositions containing mineral (clay) additives, in which for example, N-acyl amino acids, and specifically n-acyl glutamic acid amides and esters are described as gelling agents useful in lipsticks in general.

U.S. Pat. No. 5,843,194 describes another use of N-acyl glutamic acid diamide in preparing transparent candles, as a gelling agent for the nonvolatile oil-base of the candle. The candle is formed from a clear gel obtained from hydrogenated polyisobutenes of different viscosities, the N-acyl glutamic acid diamide gelling agent, and a number of further components.

Lauroyl glutamic dibutyl amide is also known from U.S. Pat. Nos. 5,362,482, and 5,266,321 to be used in water-in-oil and oily base emulsified and powdered cosmetics containing silicone oil or gel, waxes and emulsifier/gelling agents therefor, including lip treatment compositions.

There was a need, however, for a faintly colored, but essentially transparent lipstick or lip gloss composition. Therefore, it is a principal object of the present invention to provide such a composition and a method of making it.

DESCRIPTION OF THE INVENTION

The present invention related to a transparent lipstick composition which comprises (i) from about 30 to about 50% wt. tackiness agent, (ii) from about 30 to about 50% wt. of an oil or ester, (iii) from about 0.01 to about 5% wt. of a firming, bulking agent, (iv) from about 0.5 to about 10% wt. of a oil-gelatinizing agent, and (v) optionally one or more of a coloring, perfuming, and appearance improving additive.

In the lipstick composition the oil-gelatinizing agent is an amino acid gelatinization agent, more particularly an N-acyl glutamic acid diamide, such as the diamide sold by Ajinomoto Co., Inc. under the trade designation GP-1.

In the lipstick composition of the present invention the firming, bulking agent is suitably hydroxystearic acid or polyethylene, and said tackiness agent is a tacky $C_{2-14}$ polyolefin compound, such as polybutene.

The lipstick composition of the present invention suitably also includes from about 0.5 to about 5% wt. of a moisturizer, such as octyl dodecyl ricinoleate.

Thus an example of the lipstick composition of the present invention is prepared from about 40% wt. polybutene, from about 40% wt. trimethylolpropane triisostearate, a tackiness reducing oil, about 4% wt. diisostearyl maleate feel enhancing ingredient, about 4% wt. hydroxystearic acid as a solidifier, firming agent, about 0.7% wt. polyethylene as bulking agent, and about 5% wt. GP-1, together with small amounts of color additive(s), fragrance and pearlizing additive.

Suitably from about 0.01% to about 1% wt. of pigment can be used to maintain suitable transparency of the lipstick. FD&C Blue 1 (aluminum lake), or Red 7 (Ca lake), or Red 6 (Ba lake) can be most suitably employed.

I claim:

1. A wax free lipstick composition comprising (i) from about 30 to about 50% wt. tackiness agent, (ii) from about 30 to about 50% wt. of an oil or ester, (iii) from about 0.01 to about 5% wt. of a firming, bulking agent, (iv) from about 1 to about 10% wt. of a transparent, oil-gelatinizing agent, and (v) optionally one or more of a coloring, perfuming, and appearance improving additive.

2. The lipstick composition of claim 1, wherein said transparent, oil-gelatinizing agent is an amino acid gelatinization agent.

3. The lipstick composition of claim 2, wherein said amino acid gelatinization agent is an N-acyl glutamic acid diamide.

4. The lipstick composition of claim 1, wherein said firming, bulking agent is one or more of hydroxystearic acid, and polyethylene.

5. The lipstick composition of claim 4, wherein said tackiness agent is a tacky $C_{2-14}$ polyolefin compound.

6. The lipstick composition of claim 5, wherein said polyolefin compound is polybutene.

7. The lipstick composition of claim 1, further comprising from about 0.5 to about 5% wt. of a moisturizer.

8. The lipstick composition of claim 7, wherein said moisturizer is octyl dodecyl ricinoleate.

9. The lipstick composition of claim 1, further comprising from about 0.01 to about 1% wt. of a pigment.

10. The lipstick composition of claim 9, wherein said pigment is an FD&C lake.

11. The lipstick composition of claim 1, which comprises from about 30 to about 50% wt. of polybutene, from about 30 to about 50% wt. trimethylolpropane isostearate, from about 0.1 to about 0.5% wt. hydroxystearic acid, from about 0.01 to about 2% wt. polyethylene, from about 0.01 to about 2% wt. N-acyl glutamic acid diamide, and one or more of a color, fragrance, and appearance improving additive.

12. The lipstick composition of claim 11, further comprising from about 1 to about 6% wt. diisostearyl maleate as a feeling enhancer.

13. The lipstick composition of claim 9, wherein said appearance improving additive is a pearl appearance additive.

* * * * *